United States Patent [19]

Daellenbach et al.

[11] 4,010,369

[45] Mar. 1, 1977

[54] METHOD FOR RAPID PARTICLE SIZE ANALYSIS BY HYDROSIZING AND NUCLEAR SENSING

[75] Inventors: Charles B. Daellenbach; Warren M. Mahan, both of Burnsville, Minn.

[73] Assignee: The United States of America as represented by the Secretary of the Interior, Washington, D.C.

[22] Filed: Jan. 29, 1974

[21] Appl. No.: 438,152

[52] U.S. Cl. .............................. 250/356; 250/304; 250/308

[51] Int. Cl.² .......................................... G01F 1/00

[58] Field of Search ............... 210/512 M; 209/211, 209/111.5; 73/432 PS; 250/304, 435, 356

[56] References Cited

UNITED STATES PATENTS

| | | | |
|---|---|---|---|
| 3,166,496 | 1/1965 | Kelsall | 210/512 M |
| 3,255,881 | 6/1966 | Holderreed | 209/111.5 |
| 3,449,567 | 6/1969 | Oliver | 73/432 PS |
| 3,469,095 | 9/1969 | Starnes | 250/304 |
| 3,505,519 | 4/1970 | Fleming et al. | 250/304 |
| 3,519,353 | 7/1970 | Franz et al. | 73/432 PS |
| 3,718,819 | 2/1973 | Miksitz | 250/356 |
| 3,719,089 | 3/1973 | Keisall et al. | 73/432 PS |

*Primary Examiner*—Harold A. Dixon
*Attorney, Agent, or Firm*—Thomas Zack; Donald R. Fraser

[57] ABSTRACT

A method and apparatus to practice the method for rapidly determining the size and mass distribution of a sample of randomly sized particles of a known total mass. A series of substantially identical hydrocyclones are connected by conduits to each other and to a temperature controlled water feed. By restricting the cross-sectional areas of these conduits to progressively smaller values, the slurry containing the sample particles is caused to increase its velocity as it moves from hydrocyclone to hydrocyclone. As described by the Stokesian theory which relates particle diameter and settling velocity, the largest sized particles are suspended in the closed apex of the first hydrocyclone with smaller sized particles, in given size ranges, being suspended in the next succeeding hydrocyclone's apexes. In this manner, the particles are separated into discrete fractional sizes with a residual slurry of the very smallest particles being discharged. Before the discrete fractions of particles are suspended in their hydrocyclone apexes, a combined photon source, like a gamma ray source, and detector are calibrated with the water temperature kept constant. When the suspension of particles takes place, an attenuation of the radiation from the source is observed at the detector. This attenuation can be related to the mass or weight of the discrete fractions of suspended particles. Electronic circuitry is used to indicate what this fractional mass or weight is as it relates to the total weight of the sample.

6 Claims, 4 Drawing Figures

METHOD FOR RAPID PARTICLE SIZE ANALYSIS BY HYDROSIZING AND NUCLEAR SENSING

BACKGROUND OF THE INVENTION

This invention relates to the method and apparatus for determining the size and mass distribution of a randomly sized sample of particles. More specifically, our invention uses a series of liquid-cyclones and a radiation attenuation detector to arrive at the discrete fractions of particle mass and size separated.

In the mining and metallurgy field, rapid determination of the size and mass distribution of a random size sample of particles is important for several reasons. For many processes, knowledge of the size and mass of particles is a critical factor in monitoring, controlling, and optimizing the performance. For example, in the mineral beneficiation industry where comminution, the reduction of particle size, accounts for a major source of the processing costs, overgrinding can significantly increase the plant production costs; while undergrinding would not liberate the minerals and would result in lower recoveries. Since, the amount of grinding required is directly related to the size of particles involved, knowledge of this area is all important.

Our invention attempts to optimize to the smallest value the amount of comminution required by rapidly analyzing a sample of random sized particles in an on-stream control application. In the prior art, samples have been analyzed by the use of a variety of methods. Many of these methods are limited in their application because of the need for a highly dispersed and diluted feed sample, nonopacity of the fluid medium, the use of a very small sample weight which can result in processing a nonrepresentative sample, the extrapolation of size distribution from very limited data, and the use of a difficult and lengthy standardization procedure. Of the known prior art, U.S. Pat. No. 3,505,519 to M. G. Fleming et al comes the closest in its operation to our invention. However, it differs in several important features from what we will describe. The biggest differences are that we separate the randomly sized particles into discrete fractions and the method by which this is accomplished. The separation method we employ insures discretely sized fractions that are better suited for the detection step which follows.

SUMMARY OF THE INVENTION

This invention is a method and/or apparatus for determining the particle size and mass distribution of a sample of randomly sized particles of a total known weight. Initially, the random sample is separated into a series of discrete particle fractions according to their sizes. Each of these fractions then has its mass detected and this information is sent to an indicator.

The primary object of this invention is an improved system for determining the size and mass of randomly sized particles.

An additional object is to describe the steps actually taken to arrive at this determination.

Figure 1:
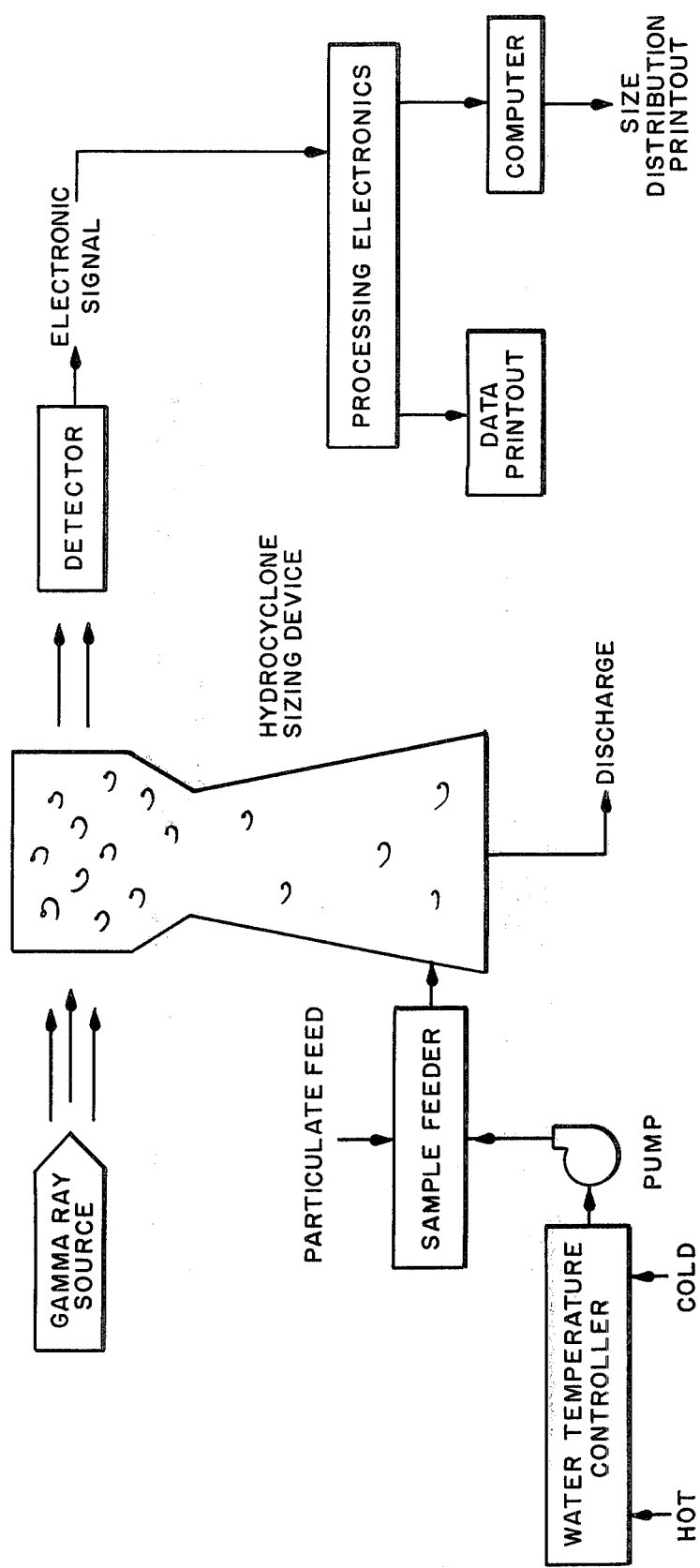
FIG. 1 is a schematic diagram of the general particulate sizing and mass sensing system arrangement.

FIG. 1 shows a schematic of the general system. Starting at the lower left hand side of the figure, it is seen that hot and cold water is fed to a water temperature controller wherein it is mixed. The purpose of this controller is to hold the mixed output water temperature constant so that reproducibility of the sought after result, to be described, is obtained. Normally, the controlled output water temperature is maintained at about 20° C with variations ranging between ±0.5° C.

This temperature controlled water is next pumped at a constant and preset flow rate to the sample feeder. At this feeder, the randomly sized particulate sample of known total weight, in a slurry form, is injected into the water to form a less dense slurry. The water flow rate during sample injection is about 1.3 times greater than final elutriation flow rate. In a typical system, the size distribution of particles ranging from the 250 micrometers (60 mesh) to seven micrometers would be determined.

The slurry of randomly sized particles is next fed at a constant flow rate to a series of interconnected hydrocyclones (cyclones). Only the first of these cyclones is shown in FIG. 1 for purposes of simplification. Except for the last cyclone which discharges into a drain, each cyclone output acts as the input into the next interconnected cyclone. The largest particles of the slurry within a given size range are suspended in the apex chamber of the first cyclone with progressively smaller size ranges of particles being suspended in the following cyclones. Particles whose size are smaller than the suspended lowest range size of the last cyclone are not recovered and are discharged into a drain.

Continuing with the explanation of FIG. 1, a high energy radiation source is placed on one side of the cyclone's apex chamber. A detector is placed opposite this source to detect the attenuation of the radiation. Preferably the radiation source is of the nonparticulate type, like gamma or X-rays, such that it emits high energy photons having no rest mass. In the actual working embodiment, two millicuries of Americium-241 were chosen as the gamma source because of its stability, long half-life of 458 years, and its high abundance of 60,000 electron volt, and gamma ray energy. The detector used was a sodium iodide thallium-activated scintillation crystal connected to a photomultiplier tube and other electronic components. The processing electronics of FIG. 1 receives the detected attenuated signal from the detector in the form of a multi pulse signal. A digital rate meter counts the pulses and visually indicates the results on a data printout and plotting recorder. The end result informs an observer of the percentage of mass (or weight) that can be attributed to each discrete fraction contained in the individual cyclones.

Figure 2:
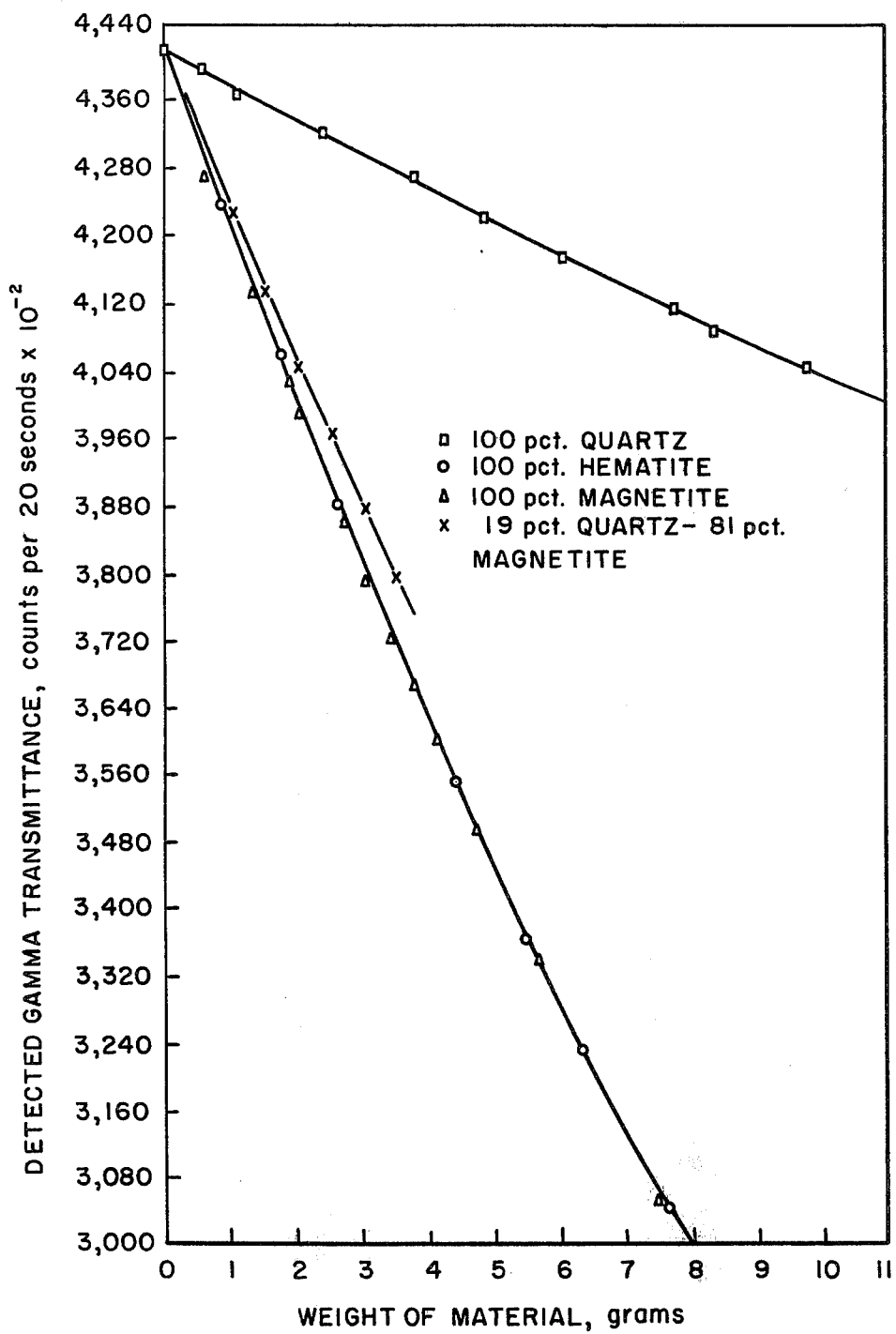
FIG. 2 shows graphs of the detected gamma transmittance versus the weight of particles under observation for three pure materials and one bimaterial.

The data graphically shown in FIG. 2 is presented to obtain a better understanding of how the detected gamma transmittance is related to the weight or mass of the particular materials under observation. Four different sets of data are involved. Three relate to the pure minerals of quartz, hematite, and magnetite. The fourth set of data is for a mixture of 19 percent quartz and 81 percent magnetite. All data shown were derived from the third hydrocyclone and are typical of data from all of the series of five hydrocyclones. Certain observations can be made from these graphs. First, it is apparent that the gamma ray attenuation is about the same for hematite and magnetite and greater than that for quartz, i.e., quartz allows more gamma transmittion for a given weight of material. The bimineral transmittance value fell somewhere between the transmittance of its two material components with the line being close to the relationship for magnetite which makes up 81 percent of the mixture.

Figure 3:
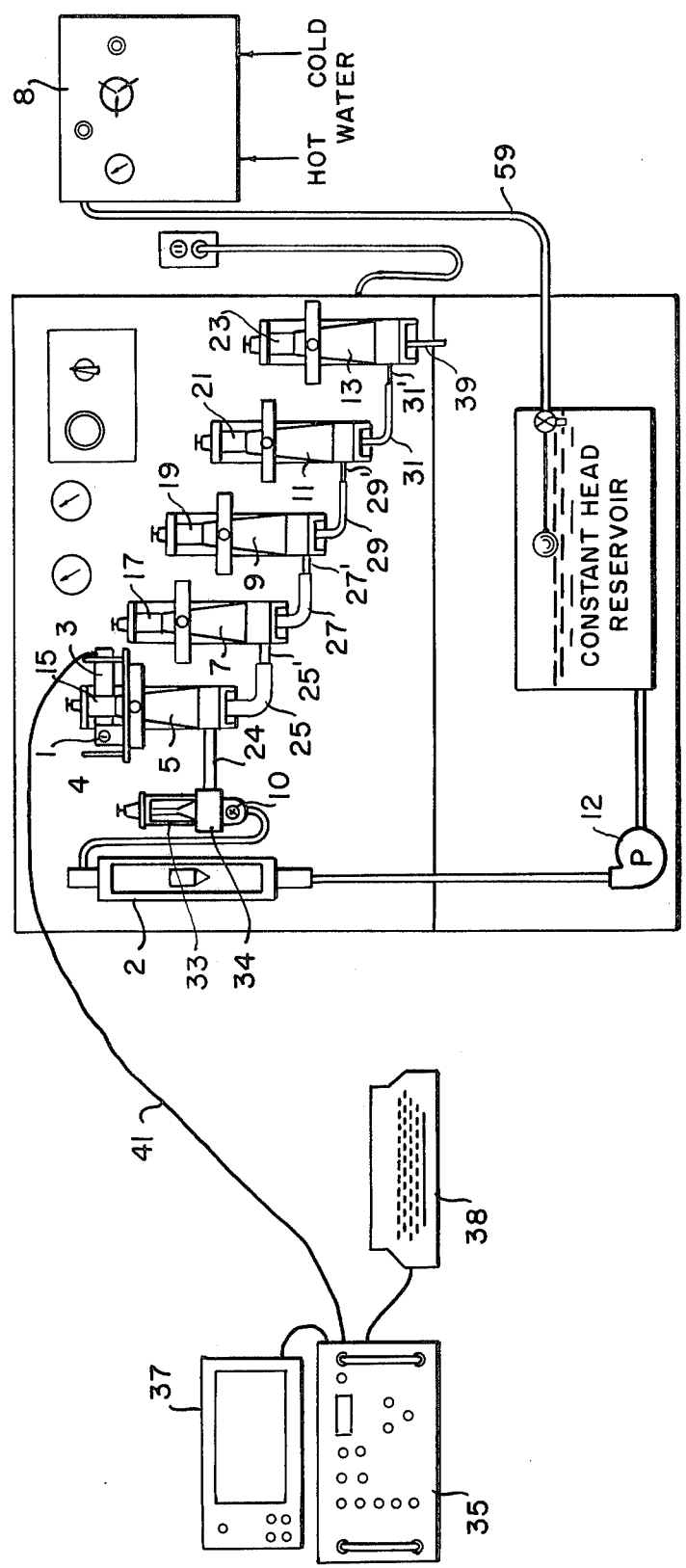
FIG. 3 shows the particulate sizing and mass sensing system arrangement in more detail.

FIG. 3 shows one type of apparatus arrangement which can be used to accomplish what was described with respect to the FIG. 1 schematic drawing. Water from temperature controller 8 is delivered at a constant and preset temperature to a constant head reservoir. From there it is pumped by pump 12 through water flow rate meter 2. This meter feeds the sample mixing assembly 34 which is in turn connected by tube 24 to the input of first hydrocyclone (cyclone) 5. Liquid conduits 25—25', 27—27', 29—29', and 31—31' interconnect the five cyclones designated by numbers 5, 7, 9, 11, and 13. Beginning with cyclone 5, these cyclones will also be referred to as the first, second, third, fourth, and the last cyclones, respectively.

Each of these five hydrocyclones is substantially identical in size, shape, function, and construction. Each cyclone is conically shaped at its lower base and inwardly tapers to where it meets a closed apex chamber in its upper portion. Tangential liquid inlets are provided for with tubes 24, 25', 27'29', and 31' at the periphery of the base with liquid outlets located at the center of the bottom of each cyclone. The interconnecting conduits between the cyclones are restricted immediately before the inlets to the next cyclones to allow the liquid flow to be progressively increased in velocity, thus the lowest velocity occurs at the inlet to the first cyclone and highest at the inlet to last cyclone. The primed numbers 25', 27', 29', and 31' indicate that these portions are smaller in cross section than those portions bearing the same unprimed numbers.

Additional equipment in the FIG. 3 illustration includes the sample container 33 into which the randomly sized particles of known total weight are initially placed; sample mixing assembly 34; data processing electronics 35 with its visual display; strip recorder 37; input/output telecommunication equipment 38; and liquid discharge tube 39, equal in diameter to primed conduit section 31', from the last cyclone.

Figure 4:
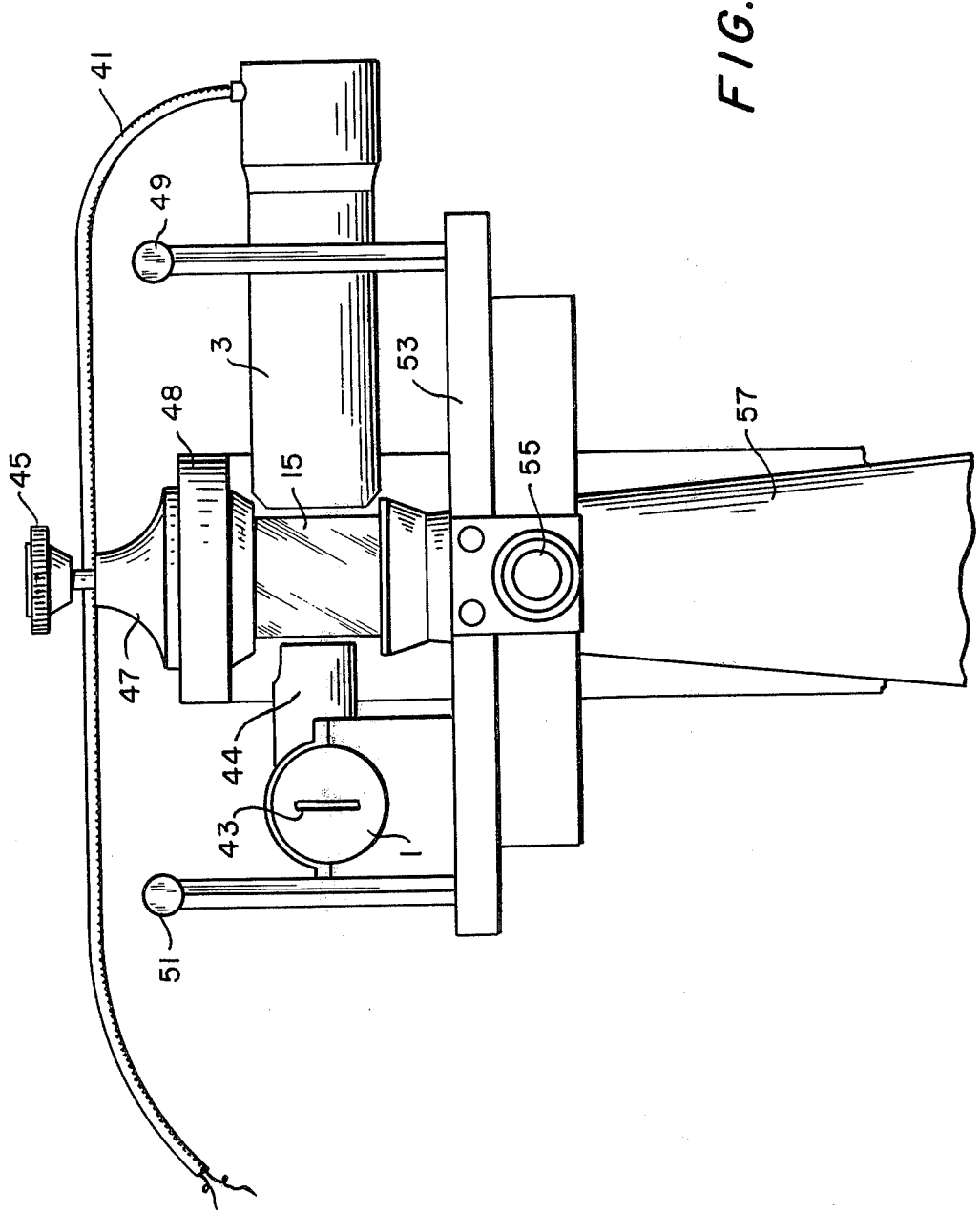
FIG. 4 illustrates the combined source and detector with one hydrocyclone in an operative state.

FIG. 4 is an enlarged view of the detecting means and separating means shown generally in FIG. 3. The detecting means consists of the radiation source 1 and the radiation detector 3. This detector is used to detect the unattenuated gamma radiation and thus allow prediction of the mass of the discrete fraction of speareated particles suspended in each of the five apex chambers. Power to run the detector and attenuation data developed by the detector are carried by wires 41. The source and detector are rigidly mounted as a single unitary unit on horizontal platform 53. Rotatable lock nut 55 on this platform allows the detector means to be secured in place to a stationary mount located adjacent to each of the five hydrocyclones. By loosening nut 55, the detecting means can be moved as a unit from cyclone to cyclone so that the suspended mass may be individually determined for each discrete fraction suspended in its apex chamber. The two U-shaped brackets 49 and 51 are handles attaching to platform 53 and allow easy movement of detector-platform assembly from detection position to detector position. As previously pointed out, the material for the gamma ray radiation source can be Americium-241. It is rigidly housed in a rotatable lead cylinder and moves with the cylinder. When a key is inserted in slot 43, the cylinder can be rotated to expose the radioactive source to an aperture in the cylinder housing 44 that faces towards the cyclone apex chamber. The separating means of FIG. 3 are the individual hydrocyclones. The ring bracket 48 of the valve casing 47 holds the cyclone in its stationary mount. The screw threaded knob 45 is used to vertically move a valve member at the top of the apex chamber to allow the suspended particles to be flushed from the chamber after the particulate mass has been determined.

Before getting into more details on the operation of the system, a brief comment on the theory of operation is appropriate. Separation of the particles according to their size is accomplished by a series of elutriation steps and is based on the Stokesian theory which relates particle diameter to its settling velocity. As such, it is a dynamic separation, dependent on such factors as the specific gravity of the particles involved; the flow velocity of the slurry; the shape of the particles; and the viscosity of the water. The operating time (elutriation time) also determines the completeness of the size operation. By keeping the water temperature constant (by control apparatus 8), the viscosity of the water can be kept constant. Mathematically, the Stokes' equation which states the relationship between the free falling velocity and the diameter of a spherical particle falling under the influence of gravity is expressed as follows:

$$v = \frac{d^2 g (\sigma - \rho)}{18 \eta} \qquad (1)$$

where $v$ = free falling velocity (cm/sec)
$d$ = particle diameter (cm)
$g$ = acceleration due to gravity (cm/sec/sec)
$\sigma$ = particle density (g/cm$^3$)
$\rho$ = fluid density (g/cm$^3$)
$\eta$ = fluid viscosity (poise)

Physically, as the slurry enters the first cyclone, it does so tangentially to the cyclone's internal surface, resulting in a force being applied to the particles outwardly directed about 90° from the force of gravity. This causes the particles to move in a swirling action to the inside wall of the inverted cone-shaped cyclone, up this wall and into the apex chamber. When the particles reach the apex chamber, they circulate down the middle of the cyclone. However, according to the Stokesian principles, only the larger particles will be sufficiently accelerated to the wall of the cyclone to be retained in the cyclone. This action of the circulating larger particles can be thought of as a dynamic suspension. Meanwhile, the smaller particles with diameter less than some limiting size are discharged through the outlet located in the center of the bottom of the cyclone 5. These smaller particles are conducted via tube 25, at the same velocity they had when entering cyclone 5, to the restricted portion 25', before the inlet to the cyclone 7, both liquid and particle velocities are increased. This results in more tangential force being applied to the particles in the slurry as it enters the next cyclone. The velocity of the liquid entering through 25' and exiting through 27 is the same. As it passes into portion 27', the velocity is again increased. The input velocity and output velocity of the slurry is constant for each cyclone. After each cyclone has dynamically suspended the particles for a given size range, particles below the lowest value of the smallest range are discharged via tube 39. To get an idea of the size range of the particles suspended in each cyclone, the following example for pure quartz particles was observed:

|  | Equivalent Stokesian Diameters - Micrometers |
|---|---|
| 1st. cyclone | 250 to 40 |
| 2nd. cyclone | 40 to 30 |
| 3rd. cyclone | 30 to 22 |
| 4rd. cyclone | 22 to 15 |
| Last cyclone | 15 to 12 |

The accuracy of the readings for the first cyclone is within one micrometer while those of the other cyclones are within one-half micrometer. particles below the 12 micrometer value are lost from the last cyclone and are not recovered.

The detection of the mass (or weight) of the discrete fractions of particles suspended in the cyclone apex chambers is accomplished by a highly sensitive nuclear densitometer. This meter consists of a source and detector in combination with the necessary electronic data processing equipment. The mass of particulate solids located within each apex chamber is directly related to the attenuation of the gamma ray beam by the solids. Mathematically, the relationship has been shown to be:

$$I = I_o e^{-\mu \rho X}$$

where $I_o$ is the intensity of the incident beam before attenuation by particulates; $I$ the intensity of the transmitted beam after attenuation by particles; $x$ the distance the beam has traversed before its attenuation is detected; $\mu$ the mass absorption coefficient of the attenuating material; and $\rho$ the density of the material. (See the book entitled "Instrument Practice" and the article "Some Applications of Radioisotopes in Instrument Engineering" by J. R. Rhodes, May 1972, pgs. 559-567 for more details). At the detector, the gamma rays are incidented upon a scintillation crystal and the value of I is detected by a photo-multiplier tube and converted to a pulse count proportion to the intensity.

It should be recognized that the attenuation of the gamma ray radiation is caused not only by the suspended solids but also by the geometry of apex chamber walls, the water of the slurry, and air gaps. By holding the attenuation caused by the geometry of the apparatus and the composition of the suspending medium constant equation (2) can be further simplified to read:

$$y = Ae^{-BW} \quad (3)$$

where $y =$ is the pulse count rate, $A$ is a constant that is equal to the pulse rate count with water in the cyclone and no particles in suspension, $B$ is a constant dependent on the composition of the particulates in suspension, and $W$ the weight of the particulates. The terms mass and weight W have been used interchangeably in this specification. The graphs for the pure minerals quartz, hematite, and magnetite, shown in FIG. 2 are described by equation (3) using experimentally determined values for the appropriate constants.

The detector 3 in the working embodiment consists of a sodium iodide thallium-activated scintillation crystal connected to a photomultiplier tube. When an electronic signal is generated by radiation, it is sent through a scintillation preamplifier to a linear amplifier and a single channel analyzer (SCA). The SCA is adjusted to a preset condition such that it will only pass those pulses originating from source 1, i.e., from a 60 KeV gamma ray source of Americium-241. Next, prescaling down by a factor of 10 takes place and the pulse signal is sent to a digital-rate meter where the intensity of the partially attenuated gamma beam signal is visually displayed on processor 35 and also sent to strip recorder 37 and data printer 38 for recording.

The method of using the equipment and the condition under which they operate should be described. Water temperature controller 8 is initially set at a predetermined temperature of about 20° C (±0.5°) and water pumped at a constant flow rate through the series of five cyclones. While the water temperature is stabilizing, the Americium source is rotated by inserting a key into slot 43. A beam of gamma rays is, as a result, directed through apex chamer 15 of the first cyclone. Ten gamma count-rate readings of 20 second duration are taken and averaged to give the base rate. The procedure is repeated for each of the remaining cyclones and allows constant A of equation (3) to be determined.

After the base count rate is established for each cyclone, a known weight of dispersed and suspendable solid particles are injected into the system from sample container 33. By rotating a screw knob on the top of container 33, an interior cone-shaped base valve is raised to gravity feed the sample into sizing system by dropping it into the sample mixing assembly 34. The water flow injection rate, controlled by valve 10, is about 45 percent greater than the final elutriation flow rate. A preliminary distribution of solids in the cyclones takes place as a result and after three minutes the water is reduced to a predetermined final elutriation flow rate of about 9.5 liters per minute. Sample elutriation continues for an additional 20 minutes. Following elutriation, flow rate is again returned to a high setting and transmittance readings taken on each of the five apex chambers containing the discrete fractions of sized, suspended particles. To verify the correctness of the results observed during the development of the system, the solids from each of the apex chambers were discharged, collected in separate beakers, dried, and weighed. The weight of solids discharged from the last cyclone in the elutriation process is caluclated by subtracting the aggregate weights of the five cyclone fractions from the total weight of the injected sample. With this procedure, graphs similar to those shown in FIG. 2 were developed for each of the five cyclones using pure minerals. The appropriate values for the constants contained in equation (3) were determined from this data and subsequently these equations were used to predict fraction weights (termed γ-determined weight).

The following table for pure quartz gives an idea of the accuracy of the gamma (γ) detection system by comparing the fractional weights determined by system versus those found by actual weighting of the fractions:

TABLE 1

Comparison of Actual Quartz Weight with that Determined by γ-Detector System

| Hydrosizer Cone No. | Size fraction, microns | Actual[1] weight, grams | γ-Determined weight, grams | Actual percent weight | γ-Determined percent weight | Difference percent weight[2] |
|---|---|---|---|---|---|---|
| First | +46.4 | 9.10 | 9.27 | 18.20 | 18.54 | +0.34 |
| Second | −46.4 + 34.2 | 12.10 | 12.00 | 24.20 | 24.00 | − .20 |
| Third | −34.2 + 24.6 | 11.31 | 11.47 | 22.62 | 22.94 | + .32 |
| Fourth | −24.6 + 17.3 | 7.42 | 7.60 | 14.84 | 15.20 | + .36 |
| Last | −17.3 + 13.9 | 2.73 | 3.07 | 5.46 | 6.14 | + .68 |

[1]Feed to hydrosizer was 50.00 grams.
[2]Difference between γ-determined and actual weight percents.

When a bimineral mixture is analyzed, a more complex formula than (3) ($y = Ae^{-BW}$) is used. This new formula, which is an extension of (3), relates total gamma transmittance and weight of sized solids suspended in an apex chamber. An equation is developed for each of the five cyclones and they are of the following form:

$$Y_t = A_1 e^{-B_1} \left(\frac{S}{100}\right)^W + A_2 e^{-B_2} \left(1-\frac{S}{100}\right)^W - A_3$$

where $Y_t$ = the detected gamma radiation transmittance (pulse count rate) in the presence of the mineral suspension; $A_1$, $A_2$, and $A_3$ are constants dependent on the source and apparatus geometry; $B_1$ and $B_2$ are constants based on the mineral composition; $S$ is the percentage concentration of one of the mineral constituents; and $W$ the total weight of suspended solids.

Tests were run using magnetite-silica as the bimineral in which the sample weight was varied while holding the mineral ratio appropriately the same. Table 2, below, sets forth the comparison data for the third cyclone (cyclone 9) using a magnetite-silica feed sample. The table gives actual weights and fraction weights that were determined by using formula (4) with transmittance data input from the γ-detector system. An average of two percent difference was noted between actual fraction weights and those detected and computed from the γ-detector system.

TABLE 2

Comparison of Actual Weight with that Determined by γ-Detector System for Bimineral Mixture[1]

| Test No. | Actual weight, grams | γ-Determined weight, grams | Weight difference, percent | |
|---|---|---|---|---|
| | | | Av. | +2 |
| 1 | 0.98 | 1.02 | | +4 |
| 2 | 1.53 | 1.56 | | +2 |
| 3 | 2.03 | 2.09 | | +3 |
| 4 | 2.54 | 2.56 | | +1 |
| 5 | 3.03 | 3.06 | | +1 |
| 6 | 3.50 | 3.58 | | +2 |

[1]Composition third hydrocyclone material about 19 weight percent silica and 81 weight percent magnetite.

The values for constants, derived from single mineral tests, were substituted directly into equation (4) for the purpose of calculating γ-determined weights in Table 2. The equation was as follows for the third cyclone:

$$Y_t = 4412.6 e^{-0.0090497} \left(\frac{S}{100}\right)^W +$$

-continued $$4418.6 e^{-0.049605} \left(1-\frac{S}{100}\right)^W - 4417$$

These tests results indicate that the weight of individual fractions of large magnetite-quartz ratio feeds can be predicted to a high degree of accuracy with this model. The excellent data fit can also be interpreted as an indication of near ideal behavior of these minerals with respect to gamma ray attenuation.

The detecting means mounted on platform 53 and described in FIGS. 3 and 4 has one significant drawback, namely it must be manually moved from cyclone to cyclone station during the determination of a complete particulate size distribution. While an actual working embodiment has not yet been constructed, it is apparent the detection step could be accomplished simultaneously at each of the five cyclone apex chambers rather than moving the single detecting means from cyclone to cyclone. This could be accomplished by arranging the cyclones in a circular pattern around a single gamma source. Sampling of process streams, sample preparation and feeding of the sample to analyzer system could also be automated to allow for an industrial on-stream analyzer. Further, equipment sequencing and particulate size calculations could be handled by a computer and time clock. Thus, full sample cycle time in a 10 to 15 minute period could be easily accomplished within the present state-of-the-art and is contemplated by this invention.

None of the specifically disclosed embodiments or disclosed uses should be used to limit the scope and extent of this invention which is to be measured only by the scope and spirit of the claims that follow.

We claim:
1. A system for determining the particle size and mass distribution of a sample of randomly sized particles from a known total mass comprising:
 a series of interconnected liquid cyclones for separating the randomly sized particles into a series of discrete fractions according to their size, said particles being fed into said cyclones in a liquid slurry at a controlled velocity;
 said interconnections comprising a series of conduits that are progressively smaller in cross-sectional area between any two liquid cyclones when measured perpendicular to the liquid flow;
 means for detecting the particle mass of each of said discrete size fractions; and
 means for indicating the detected mass of said fractions.

2. A system for determining the particle size and mass distribution of a sample of randomly sized particles from a known total mass comprising:
- a series of interconnected liquid cyclones for separating the randomly sized particles into a series of discrete fractions according to their size;
- said particles being fed into said cyclones in a liquid slurry at a controlled velocity;
- each of said liquid cyclones being substantially identical containers in shape and size with the largest sized particles being retained in the first container into which the liquid flows;
- said interconnections between adjacent connected liquid cyclones comprising a conduit whose cross-sectional area is greater at the output of one liquid cyclone than it is at the input to the next connected liquid cyclone;
- means for detecting the particle mass of each of said discrete size fractions; and
- means for indicating the detected mass of said fractions.

3. A system for determining the particle size and mass distribution of a sample of randomly sized particles from a known total mass comprising:
- a series of interconnected liquid cyclones for separating the randomly sized particles into a series of discrete fractions according to their size;
- said particles being fed into said cyclones in a liquid slurry at a controlled velocity;
- said interconnections between liquid cyclones having means for increasing the velocity of the slurry as it flows from one cyclone to the next to provide for the retention of the largest particles at the first cyclone into which the slurry flows and the retention of progressively smaller particles at each succeeding cyclone;
- means for detecting the particle mass of each of said discrete sized fractions; and
- means for indicating the detected mass of said fractions.

4. A system for determining the particle size and mass distribution of a sample of randomly sized particles from a known total mass comprising:
- means for separating these randomly sized particles into a series of discrete fractions according to their size, said separating means comprising a series of interconnected liquid cyclones into which said randomly sized particles are fed in a liquid slurry at a controlled velocity, wherein the interconnections between liquid cyclones comprises a series of conduits with the conduits being progressively smaller in cross-sectional area between any two liquid cyclones when measured perpendicular to the liquid flow;
- means for detecting the particle mass of each of said discrete size fractions; and
- means for indicating the detected mass of said fractions.

5. A system for determining the particle size and mass distribution of a sample of randomly sized particles from a known total mass comprising:
- means for separating the randomly sized particles into a series of discrete fractions according to their size, said separating means comprising a series of interconnected liquid cyclones into which said randomly sized particles are fed in a liquid slurry at a controlled velocity; wherein each of said liquid cyclones are containers substantially identical to each other in shape and size with the largest sized particles being retained in the first container into which the liquid flows, and the interconnections between each adjacent connected liquid cyclone comprises a conduit whose cross-sectional area is greater at the input to the next connected liquid cyclone;
- means for detecting the particle mass of each of said discrete size fractions; and
- means for indicating the detected mass of said fractions.

6. A system for determining the particle size and mass distribution of a sample of randomly sized particles from a known total mass comprising:
- means for separating the randomly sized particles into a series of discrete fractions according to their size, said separating means comprising a series of interconnected liquid cyclones into which randomly sized particles are fed in a liquid slurry at a controlled velocity, wherein the interconnections between liquid cyclones have means for increasing the velocity of the slurry as it flows from one cyclone to the next to provide for the retention of the largest particles at the first cyclone into which the slurry flows and the retention of progressively smaller particles at each succeeding cyclone;
- means for detecting the particle mass of each of said discrete size fractions; and
- means for indicating the detected mass of said fractions.

* * * * *